United States Patent [19]  [11] 4,222,960
Wechsberg et al. [45] Sep. 16, 1980

[54] PROCESS FOR THE MANUFACTURE OF α-HYDROXYCARBOXYLIC ACID AMIDES

[75] Inventors: Manfred Wechsberg, Linz; Rupert Schönbeck, Leonding, both of Austria

[73] Assignee: Chemie Linz Aktiengesellschaft, Linz, Austria

[21] Appl. No.: 45,677

[22] Filed: Jun. 5, 1979

[30] Foreign Application Priority Data

Aug. 6, 1978 [DE] Fed. Rep. of Germany ....... 2825267
Dec. 6, 1978 [AT] Austria ................................. 4248/78

[51] Int. Cl.² ................. C07C 103/127; C07C 103/26
[52] U.S. Cl. ............................. 260/559 R; 260/561 B
[58] Field of Search ........................ 260/561 B, 559 R

[56] References Cited
U.S. PATENT DOCUMENTS

| 2,229,897 | 1/1941 | Migrdichian | 260/561 B |
| 3,166,588 | 1/1965 | Johnson | 260/561 B |
| 3,190,916 | 6/1965 | Rainer | 260/561 B |
| 3,366,639 | 1/1968 | Haefele | 260/295 |
| 3,781,351 | 12/1973 | Fenton | 260/561 B |
| 4,018,829 | 4/1977 | Gruber et al. | 260/561 B |

FOREIGN PATENT DOCUMENTS 2454497 5/1976 Fed. Rep. of Germany .
852664 10/1960 United Kingdom .

Primary Examiner—Arthur P. Demers
Attorney, Agent, or Firm—Wenderoth, Lind & Ponack

[57] ABSTRACT

Process for the manufacture of α-hydroxycarboxylic acid amides by adding water onto cyanohydrins in an aqueous medium containing 10–60% by weight of the oxo compound on which the cyanohydrin is based, with the aid of a catalyst dissolved in the reaction medium and selected from the group consisting of alkali metal-, alkaline earth metal- and alkylammonium salts of boric acid, at a pH from 7–11.

8 Claims, No Drawings

PROCESS FOR THE MANUFACTURE OF α-HYDROXYCARBOXYLIC ACID AMIDES

The present invention relates to a process for the manufacture of α-hydroxycarboxylic acid amides by adding water onto cyanohydrins catalytically in the presence of oxygen-containing boron compounds.

The addition of water onto carboxylic acid nitriles to give carboxylic acid amides with the aid of concentrated sulfuric acid has been known for a long time and is used on a large industrial scale, for example, in the manufacture of acrylamide from acrylonitrile. However, since more than 1 mole of sulfuric acid must be used per mole of nitrile in this process, and furthermore a salt-like addition compound, from which the amide must be isolated by neutralizing the mineral acid, is intermediately formed, catalytic processes for the direct manufacture of carboxylic acid amides from nitriles have been developed recently. Catalysts based on copper, such as copper/chromium oxides, copper/molybdenum oxides, copper oxides or Raney copper, have proved particularly suitable in these processes and are already of significance on a large industrial scale (Kirk-Othmer, volume 1 (1978), 303).

However, if an α-hydroxynitrile is to be used to prepare the corresponding α-hydroxyamide, even the most active of these copper catalysts are ineffective. Only manganese dioxide gives, in the case of the hydratisation of acetone cyanohydrin, according to the U.S. Pat. No. 3,366,639, results which are to some extent useful. Nevertheless, it is known from U.S. Pat. No. 4,018,829, which appeared a short time ago, that the catalytic activity of manganese dioxide depends to a greater or lesser extent on its modification. In particular, according to this Patent, δ-manganese dioxide, which is a largely amorphous modification of manganese dioxide, is very particularly suitable, but the use of this δ-manganese dioxide, which is not obtainable commercially and the manufacture of which is effected from potassium permanganate and hydrogen peroxide according to the instructions by O. Glemser et al., Z.anorg.allg.-Chemie, 309 (1961/12), appears to be associated with considerable effort. Apart from the relatively expensive manufacture of the catalyst, heterogeneous catalysis is also always beset with problems of separating off the finely divided catalyst from the reaction solution (for example by filtration) or, for example, also with erosion problems during the reaction.

Surprisingly, it has now been found that the addition of water onto cyanohydrins with formation of α-hydroxycarboxylic acid amides is possible by homogeneous catalysis in the presence of simple boron compounds which are frequently manufactured on a large industrial scale, such as borax, perborax or other salts of orthoboric acid, like the alkali metal-, alkaline earth metal- or alkylammonium salts.

The present invention accordingly relates to a process for the manufacture of α-hydroxycarboxylic acid amides from cyanohydrins by adding on water catalytically, which is characterized in that the water is added on in an aqueous reaction medium which contains between 10 and 60 per cent by weight of the oxo compound on which the cyanohydrin is based, in the presence of a catalyst dissolved in the reaction mixture and consisting of oxygen-containing boron compounds, at a pH value of 7 to 11.

More particularly, the invention relates to a process for the manufacture of an α-hydroxycarboxylic acid amide of the formula

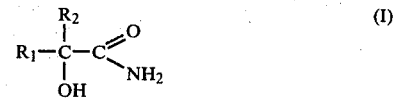

in which $R_1$ is hydrogen or straight chain or branched alkyl with 1–4 carbon atoms and $R_2$ is alkyl with 1–6 carbon atoms or phenyl, comprising reacting a cyanohydrin of the formula

in which $R_1$ and $R_2$ are as defined above in an aqueous reaction medium having a pH value of 7–11 and containing from 10 to 60% by weight of an oxo compound of the formula

in which $R_1$ and $R_2$ have the same meaning as in the cyanohydrin of the formula (II) used, in the presence of a catalyst, dissolved in the reaction medium, selected from the group consisting of alkali metal-, alkaline earth metal- and alkylammonium salts of boric acid.

In the process of the invention cyanohydrins derived from aliphatic aldehydes or ketones or from aromatic aldehydes may be used. Particularly suitable are cyanohydrins derived from aldehydes or ketones having from 3 to 10 carbon atoms, such as acetone, methylethylketone, diethylketone, methylheptylketone or isobutyraldehyde. Aromatic aldehydes like benzaldehyde are also preferred.

The oxygen-containing boron compounds used as the catalyst are employed at a pH value of 7 to 11 since they lose their activity in the acid range. Alkali metal salts or alkaline earth metal salts of orthoboric acid or metaboric acid, such as, for example, sodium borates, potassium borates and calcium borates, are used. Salts which are manufactured on a large industrial scale, such as borax or perborax, are preferred. However, it is also possible to produce such salts in situ, by adjusting boric acid itself to the pH value optimum for hydratisation of the cyanohydrin concerned by adding sodium hydroxide solution or potassium hydroxide solution (the choice of base will depend, inter alia, also on the solubility properties of the borate formed. For example, a mixture of boric acid with 5 to 80% by weight of NaOH can be used as the catalyst.

Special results are also obtained by using alkylammonium salts of boric acid. In this case the alkylamine is added to the boric acid until the required pH is reached. Particularly suitable alkylamines are tertiary or secondary alkylamines, preferably amines containing alkyl groups with 1–6 carbon atoms, such as triethylamine, diethylamine, dimethylamine or di- and triisopropylamine. For example, a mixture of boric acid with 10 to 70% by weight of triethylamine can be used as the catalyst.

If borax or other borates which have an alkaline reaction in aqueous solution are used, re-adjustment of the pH can in general be omitted. Possible side reactions are largely suppressed by adding to the reaction mixture an oxo compound on which the cyanohydrin is based. The weight ratio of oxo compound to water can be chosen as desired, as long as the catalyst has an adequate solubility and the concentration is not so small that industrially useless space/time yields result. The reaction is carried out in a reaction medium which contains 10 to 60% by weight of oxo compound.

The remaining reaction conditions, such as temperature and concentration ratios of the reactants are of secondary importance and can be chosen in an appropriate range such that the catalyst dissolves in the reaction mixture and optimum conversion, yield and purity of the desired amide are achieved. For example, the catalyst can be used in a concentration of 0.1 to 5% by weight, and the reaction can be carried out at temperatures between 30° and 100° C., or more particularly, between 50° and 70° C.

For carrying out the process according to the invention, the suitable amount of boron compound is added to a mixture of the cyanohydrin, water and the oxo compound and the reaction mixture is warmed to the reaction temperature. If, for example, boric acid is used as the catalyst, this is dissolved in water and the solution is adjusted to a pH value of between 7 to 11 with a base. When the reaction has ended, the volatile constituents, namely the oxo compound, water and unreacted cyanohydrin, are distilled off from the reaction medium and are used for the next batch, while the residue is extracted with an organic solvent, such as, for example, acetone. The extraction residue thereby formed is essentially the boron compound employed as the catalyst and can be re-used for further reactions, while after evaporation of the extraction agent, the extracted $\alpha$-hydroxycarboxylic acid amide can be further used directly or can be purified by recrystallization.

The important point of the present process is that, with the aid of a very simple and cheap catalyst, a cyanohydrin, such as, for example, acetone cyanohydrin, can be used to manufacture, by homogeneous catalysis, $\alpha$-hydroxyisobutyramide. No filtration steps from Cu compounds or $\delta$-manganese dioxide are necessary. Methacrylic acid esters can then be manufactured by esterification and dehydratisation by known processes (compare German Offenlegungsschrift No. 2,454,497 and GB-Patent No. 852.664). The other amides which can be manufactured by the process according to the invention are also valuable intermediate products. They can be used, for example, for obtaining various $\alpha$-hydroxycarboxylic acid derivatives and $\alpha$-$\beta$-unsaturated carboxylic acid derivatives.

In the following text, several examples which illustrate the process according to the invention in more detail are described. However, the examples given are in no way intended to limit the extent of the invention.

EXAMPLE 1

11 g of borax dried at 80° C. (content of boron: 15.0%) were added to a solution of 125 g (1.47 moles) of acetone cyanohydrin in 300 g of water and 300 g of acetone and, after warming the reaction mixture to 65° C., the borax dissolved therein completely. After a reaction time of 25 hours at 65° C., the volatile constituents (at 70° C. and 3,000 Pa) were distilled off, the resulting distillate, which contained the remaining, unreacted portions of acetone cyanohydrin, was made available for the next batch and the residue was extracted with a total of 500 ml of acetone at 56° C., whereupon a residue insoluble in acetone remained (10.5 g; boron content; 15.8%) and was used again as the catalyst for the next batch. The acetone solution was then evaporated, whereupon 127.5 g of crude $\alpha$-hydroxyisobutyramide of melting point 83°-91° C. remained. This corresponds to a crude yield, relative to acetone cyanohydrin reacted, of 92.4% of theory.

After purification by recrystallization from acetone, pure $\alpha$-hydroxyisobutyramide of melting point 90°-94° C. is obtained. The yield is 107 g, which is 77.5% of theory.

EXAMPLE 2

Completely analogously to Example 1, a further batch was reacted using the residue insoluble in acetone from Example 1 (10.5 g; 15.8% of boron) as the catalyst. The crude yield in this subsequent batch, which was reacted under the same experimental conditions as in Example 1, was 135 g, which is 96.4% of theory.

After purification by recrystallization, 110 g, which is 78.5% of theory, of pure $\alpha$-hydroxyisobutyramide, melting point: 90°-94° C., were obtained. Unreacted acetone cyanohydrin was recovered in the acetone/water mixture distilled off.

EXAMPLE 3

125 g of acetone cyanohydrin and 23.5 g of sodium perborate were dissolved in 300 g of acetone and 300 g of water and the solution was warmed to 60° C. for 25 hours. The cyanide content of the reaction solution, measured by the Liebig method, was then 1.5, compared with 9.2 at the start of the reaction, which corresponds to a degree of conversion of 90%. After distilling off the volatile constitutents at 90° C. and 2,000 Pa, the residue was treated 3 times at 50° C. with a total of 500 ml of acetone and the filtered extraction solution was concentrated to dryness at 90° C. and 2,000 Pa. 120 g of crude $\alpha$-hydroxyisobutyramide were obtained as the residue, which corresponds to a yield of 88% of theory, and can be purified by distillation or recrystallization.

EXAMPLE 4

200 g of water and 10 g of borax were added to a solution of 99 g of methyl ethyl ketone cyanohydrin and 200 g of methyl ethyl ketone and the mixture was warmed to 60° C. for 25 hours. Thereafter, the low-boiling constituents were distilled off at 90° C. and 30 mbars and the residue was extracted with acetone. Further working up was effected by distillation in vacuo, 67 g of 2-hydroxy-2-methylbutyric acid amide being obtained at 97°-104° C. and 1 mbar; this corresponds to a yield of 82% of theory, relative to cyanohydrin reacted.

EXAMPLE 5

99 g of isobutyraldehyde cyanohydrin, 250 g of water and 11 g of borax were warmed to 75° C. and the homogeneous solution was kept at this temperature for 25 hours. The reaction mixture was then freed from the volatile constituents at 90° C. and 30 mbars and the residue was extracted with boiling acetone. After cooling the extraction solution, 2-hydroxy-3-methylbutyric acid amide was obtained as crystals in a yield of 71% of theory (relative to cyanohydrin reacted).

Melting point = 99°-104° C.

EXAMPLE 6

107 g of benzaldehyde cyanohydrin, 300 g of water and 10 g of borax were reacted at 60° C. for 25 hours and the reaction mixture was then freed from low-boiling constituents at 90° C. and 30 mbars. The resulting residue was extracted with acetone and the mandelic acid amide was recrystallized from water. Melting point=131°-134° C. The yield, relative to cyanohydrin reacted, was 43% of theory.

EXAMPLE 7

11 g of boric acid were added to a solution of 125 g of acetone cyanohydrin, 300 g of water and 300 g of acetone and the pH value was adjusted to 8.9 with 3.5 g of potassium hydroxide. After 25 hours at 65° C., the reaction was interrupted, at a degree of conversion of 90.3%, and the volatile constituents, including the unreacted acetone cyanohydrin, were distilled off at 3,000 Pa. The residue was taken up in 400 g of acetone, the mixture was filtered and the acetone was distilled off from the filtrate. The crude product (136 g) thus obtained was distilled in vacuo for purification. The yield was 116 g, which corresponds to 84.7% of the theoretical yield of 136.8 g. According to $NH_3$ analysis, the $\alpha$-hydroxyisobutyramide was 97.1% pure.

EXAMPLE 8

11 g of boric acid were added to 125 g of acetone cyanohydrin, 300 g of water and 300 g of acetone and the pH value of the mixture was adjusted to 9 with 3.2 g of sodium hydroxide. After a reaction time of 25 hours at 65° C., the volatile constituents were distilled off at 3,000 Pa and the residue was extracted with 400 g of acetone. the crude yield of $\alpha$-hydroxyisobutyramide was 130 g, which corresponds to 96% of the theoretical yield of 135.4 g, based on a conversion of 89.4%. According to the determination of $NH_3$, the crude product was 91.8% pure.

EXAMPLE 9

To 125 g of acetone cyanohydrin, 300 g of acetone and 300 g of water, 75 g of boric acid (content of boron: 17.47 %) and 57 g of triethylamine were added. The resulting solution was warmed and maintained at 65° C. for 14 hours. The degree of conversion of the acetone cyanohydrin was 95.35%. The volatile constituents of the reaction mixture were distilled off in vacuo and the residue was extracted with acetone. The acetone solution was then evaporated, whereupon 153 g of slightly colored crude $\alpha$-hydroxyisobutyramide remained. According to $NH_3$ analysis, the product was 94.1% pure.

It was recrystallized twice from acetone, whereupon 103 g of white crystals of melting point 90°-93° C., and, according to $NH_3$ analysis of 99.6 % purity were obtained.

What we claim is:

1. Process for the manufacture of an $\alpha$-hydroxycarboxylic acid amide of the formula

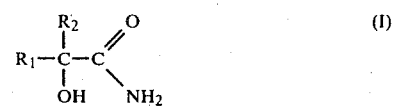

in which $R_1$ is hydrogen or straight chain or branched alkyl with 1-4 carbon atoms and $R_2$ is alkyl with 1-6 carbon atoms or phenyl, comprising reacting a cyanohydrins of the formula

in which $R_1$ and $R_2$ are as defined above in an aqueous reaction medium having a pH value of 7-11 and containing from 10 to 60 % by weight of an oxo compound of the formula

in which $R_1$ and $R_2$ have the same meaning as in the cyanohydrine of the formula (II) used in the presence of an catalyst dissolved in the reaction medium selected from the group consisting of alkali metal-, alkaline earth metal- and alkylammonium salts of boric acid.

2. Process according to claim 1 in which the catalyst is a mixture of boric acid with 5 to 80 % by weight of NaOH.

3. Process according to claim 1, in which the catalyst is borax or perborax.

4. Process according to claim 1, in which the catalyst is a mixture of boric acid with 10 to 70% by weight of triethylamine.

5. Process according to claim 1, in which the catalyst is used in a concentration of 0.1 to 5% by weight.

6. Process according to claim 1, in which the reaction is carried out at temperatures between 30° and 100° C.

7. Process according to claim 1, in which the reaction is carried out at temperatures between 50° and 70° C.

8. Process according to claim 1, in which the compound of formula (II) is acetone cyanohydrin.

* * * * *